United States Patent
Fei

(10) Patent No.: US 10,058,254 B2
(45) Date of Patent: *Aug. 28, 2018

(54) SYSTEMS AND METHODS FOR OPTICAL SENSOR ARRANGEMENTS

(71) Applicant: Physical Enterprises, Inc., Vancouver (CA)

(72) Inventor: Ming Shun Fei, Coquitlam (CA)

(73) Assignee: Physical Enterprises Inc., Vancouver, British Columbia (CA)

( * ) Notice: Subject to any disclaimer, the term of this patent is extended or adjusted under 35 U.S.C. 154(b) by 605 days.

This patent is subject to a terminal disclaimer.

(21) Appl. No.: 14/468,916

(22) Filed: Aug. 26, 2014

(65) Prior Publication Data

US 2014/0378844 A1 Dec. 25, 2014

Related U.S. Application Data

(60) Provisional application No. 61/976,388, filed on Apr. 7, 2014.

(51) Int. Cl.
*A61B 5/024* (2006.01)
*A61B 5/00* (2006.01)
*A61B 5/026* (2006.01)

(52) U.S. Cl.
CPC ........ *A61B 5/02427* (2013.01); *A61B 5/0261* (2013.01); *A61B 5/681* (2013.01); *A61B 2560/0462* (2013.01); *A61B 2562/0233* (2013.01)

(58) Field of Classification Search
None
See application file for complete search history.

(56) References Cited

U.S. PATENT DOCUMENTS

| 3,769,974 A | 11/1973 | Smart et al. |
| 4,880,304 A | 11/1989 | Jaeb et al. |
| 4,938,218 A * | 7/1990 | Goodman .......... A61B 5/04485 600/338 |
| 5,130,531 A | 7/1992 | Ito et al. |
| 5,237,994 A | 8/1993 | Goldberger |
| 7,067,893 B2 | 6/2006 | Mills et al. |

(Continued)

FOREIGN PATENT DOCUMENTS

| WO | WO2011051888 | 5/2011 |
| WO | WO2013106607 | 7/2013 |

*Primary Examiner* — Carolyn Pehlke
(74) *Attorney, Agent, or Firm* — Clayton, McKay & Bailey, PC

(57) ABSTRACT

Described herein are systems and methods for mounting optical sensors in a physiological monitoring device worn by a user to sense, measure, communicate, and/or display physiological information. The monitoring devices may be embodied as, for example, a fitness band, a bracelet, a watch, or some other wearable device such as an activity tracker, a health, wellness, or sleep monitor, or an athletic training device. The device may comprise one or more light sources and optical detectors. Optical lenses may be mounted in a face of the device for partially receiving or containing the light sources and optical detectors. The devices and methods described herein may optically isolate the light source(s) from the optical detector(s) to ensure the accurate and reliable detection and measurement of physiological information.

16 Claims, 8 Drawing Sheets

(56) References Cited

U.S. PATENT DOCUMENTS

| | | |
|---|---|---|
| 9,226,663 B2* | 1/2016 | Fei .................. A61B 5/0059 |
| 2012/0197093 A1 | 8/2012 | LeBoeuf et al. |
| 2013/0060098 A1 | 3/2013 | Thomsen et al. |
| 2013/0296714 A1* | 11/2013 | Kassim ............ A61B 5/6898 |
| | | 600/479 |
| 2014/0127996 A1* | 5/2014 | Park .................. H04W 4/027 |
| | | 455/41.1 |
| 2014/0142403 A1 | 5/2014 | Brumback et al. |
| 2014/0206976 A1 | 7/2014 | Thompson et al. |
| 2014/0221854 A1 | 8/2014 | Wai |
| 2014/0288435 A1 | 9/2014 | Richards et al. |

* cited by examiner

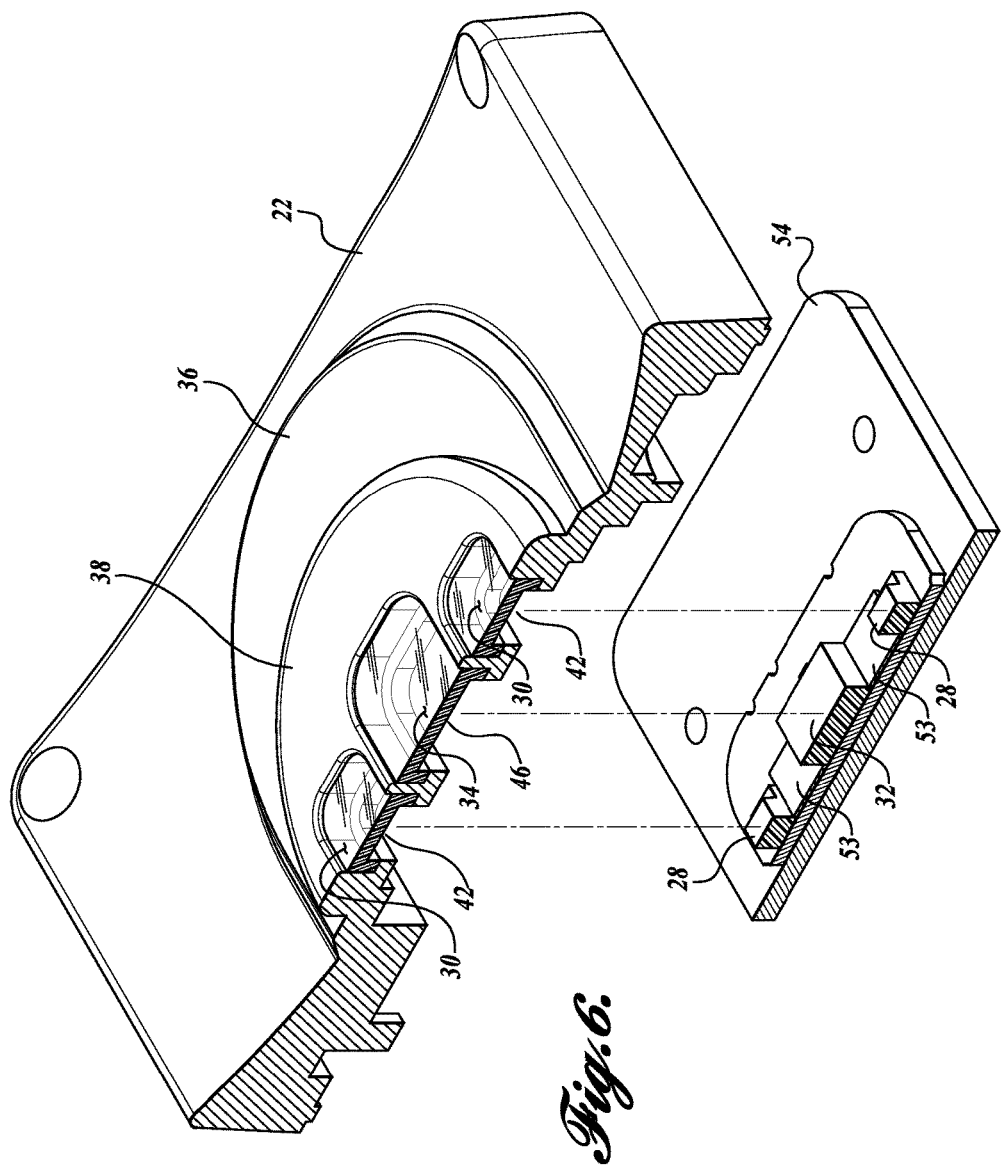

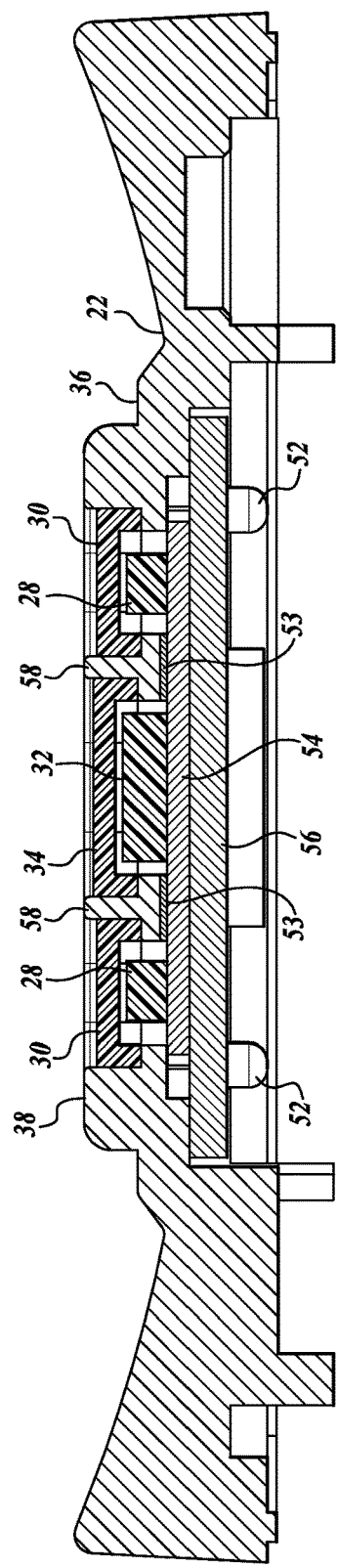

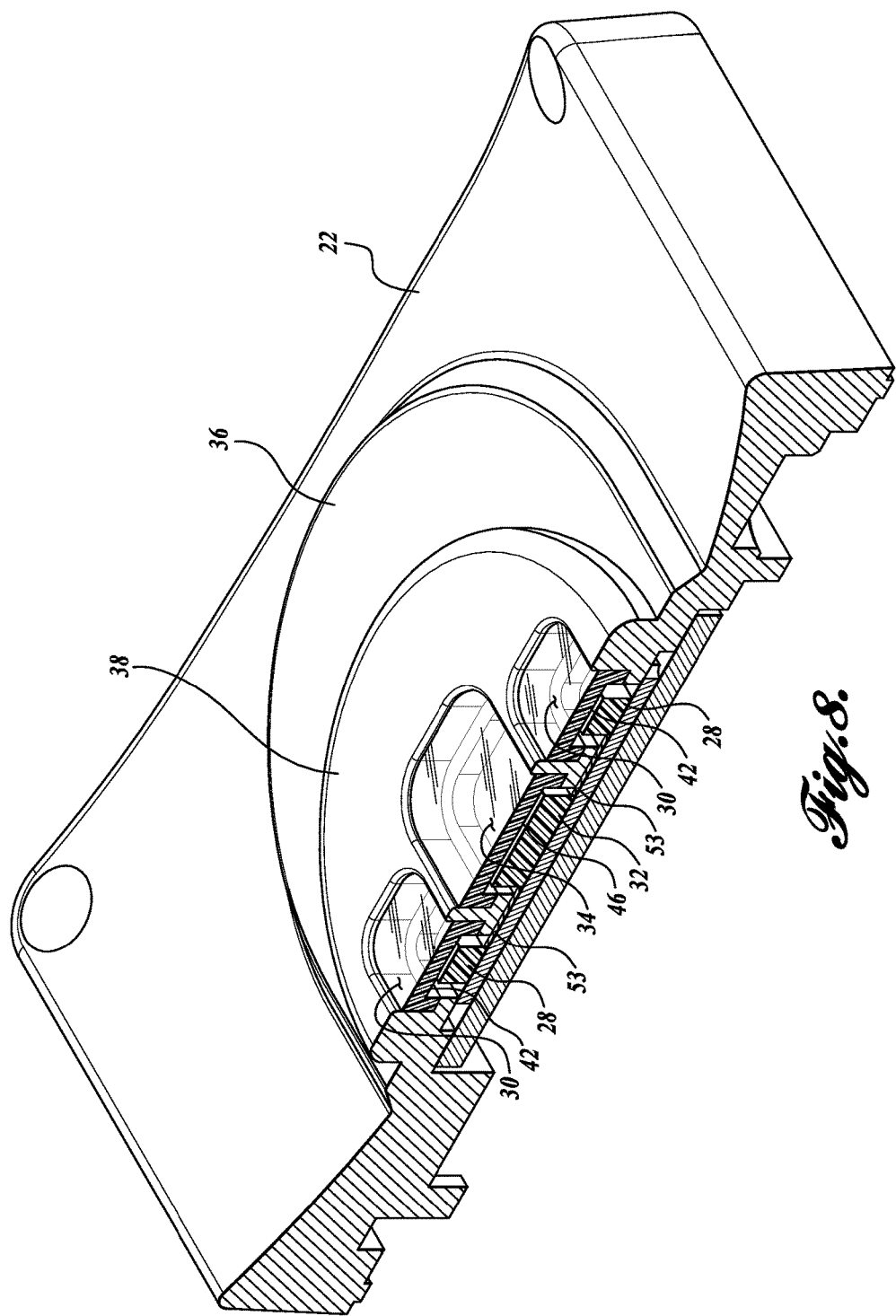

SYSTEMS AND METHODS FOR OPTICAL SENSOR ARRANGEMENTS

This non-provisional application claims the benefit of priority to U.S. Provisional Patent Application No. 61/976,388, filed Apr. 7, 2014, which is expressly incorporated herein by reference.

FIELD OF THE DISCLOSURE

The embodiments relate generally to systems and methods that use non-invasive electro-optical technology for sensing and measuring physiological parameters. More particularly, the embodiments relate to arrangements for the mounting of optical sensors in physiological monitoring devices that are worn by a user.

BACKGROUND

Numerous portable devices have been developed in which optical sensors are used to detect, measure, and display various physiological parameter information of a user. For example, some devices detect and measure the variation in blood flow through arteries or blood volume in subcutaneous tissue. Applications for such optical sensors include the monitoring of heart rate, glucose level, apnea, respiratory stress, and other physiological conditions. The optical sensor of such arrangements include one or more light sources that illuminate a targeted portion of the human body and one or more associated optical detectors that receive a portion of the optical energy emitted by the light sources. There are two basic types of such arrangements. In transmissive sensor arrangements, a relatively thin portion of the body such as the tip of the finger or the earlobe is positioned between a light source and a photo detector. Light that passes through the body tissue impinges on the photo detector resulting in an electrical signal that is synchronized to each heartbeat. In reflective sensor arrangements, a sensor that includes one or more light sources located in spaced apart juxtaposition with a photo detector is positioned against a targeted area of the body. Optical energy emitted by the light sources passes through the skin of the targeted tissue region, is scattered, partially absorbed, and is reflected by the body (e.g., blood flowing through arteries and other vascular structure). In some applications, the reflected optical energy is in effect modulated in accordance with blood flow in the targeted area and detected by the photo detector. The detected reflection can then be used to produce a signal pulse that is synchronized to each heartbeat. In both transmissive and reflective arrangements, the signal produced by the photo detectors is processed to display or otherwise provide a real time indication of the monitored physiological parameter.

One area of growing interest in the use of physiological monitors is with respect to personal wellness and/or physical exercise for purposes of fitness training and weight loss. Technological advances relating to optical sensors, signal processing, and display devices have made it possible to realize small, light-weight physiological monitors that can be embodied as armbands or bracelets that are comfortably worn by a user. For example, the embodiments described herein comprises an optical sensor that may be included in a wearable device.

Providing physiological monitors for wellness and physical exercise applications is subject to numerous design and manufacturing considerations. For example, the electronic circuitry for processing the signal produced by the photo detector and displaying an indication of the monitored parameter must operate at a low power level to provide adequate battery life while simultaneously providing sufficient accuracy. Constraints relating to the physical design of such monitors are not limited to the challenges of packaging the electronics and display units in an arrangement that can be easily and comfortably worn by a user. Special considerations and constraints are present with respect to incorporation of the optical sensor. For example, the light sources and photodiode of the optical sensor must be optically isolated from one another. Otherwise, the photo detector will receive optical energy that is not modulated by heartbeat, which can result in an unwarranted increase in electrical design requirements and/or seriously affect monitoring accuracy and power requirements. Similarly, optimal performance requires that the optical sensor be firmly positioned against the user's skin so that light emitted by an optical source passes through the skin and, additionally, so that ambient light does not reach an associated photo detector. Firmly positioning the optical sensor against the user's skin also is important with respect to preventing movement of the sensor that can affect the accuracy of the monitoring device and/or interrupt its operation. Additionally, the optical sensor should be securely retained by the monitoring device to maintain physical integrity and facilitate satisfactory waterproofing of the entire monitor.

Because of the above mentioned design and manufacturing considerations, as well as others that are known to designers and manufacturers, a need exists for improved systems and techniques for incorporating optical sensor arrangements in physiological monitoring devices. The need is of special significance relative to personal wellness, activity, sleep, and exercise monitors. In particular, the manufacturing costs of such devices must be maintained as low as possible to provide a generally affordable and competitive product without sacrificing product accuracy and quality.

SUMMARY OF THE DISCLOSURE

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

The present disclosure describes an optical sensor arrangement that may be configured for use in physiological monitoring devices that may be used for physical training, activity tracking, wellness monitoring, sleep monitoring, and/or other suitable activities. In one aspect, the optical sensor arrangement may comprise one or more optical sensor light sources and/or photo detectors. In one embodiment, the one or more light sources and/or photo detectors may be mounted in one or more transparent lenses that may be installed in a portion of a monitoring device configured for placement in contact with a user's skin. In a further embodiment, the monitor may be a wearable device comprising one or more light sources and/or photodetectors. In such an embodiment, the light sources may comprise two or more spaced apart light emitting diodes (LEDs). Each photo detectors may be a photodiode. In particular, each photodiode may be positioned between a corresponding pair of LEDs.

In another aspect, the LED(s) and the photodiode(s) may be positioned by and mounted to one or more printed circuit boards. In one embodiment, the printed circuit board, LED(s), and photodiode(s) may be installed in the interior of the device and the lenses may be positioned at or near an exterior surface of the device. In some embodiments, the device may comprise structure that may extend inwardly from the exterior of the device to contact the printed circuit in a region between the LED(s) and the photodiode(s) to prevent light emitted by the LED(s) from being directly detected by the photodiode(s). In further embodiments, a pliant opaque layer of tape or sponge-like material may also be positioned on the printed circuit board such that the inwardly extending structure may contact the opaque layer to further ensure optical isolation of the photodiode(s).

Additional objects and advantages of the present disclosure will be set forth in part in the description which follows, and in part will be obvious from the description, or may be learned by practice of the disclosure. The objects and advantages of the disclosure will be realized and attained by means of the elements and combinations particularly pointed out in the appended claims.

It is to be understood that both the foregoing general description and the following detailed description are illustrative and explanatory only and are not restrictive of the claims.

The accompanying drawings, which are incorporated in and constitute a part of this specification, illustrate several embodiments and together with the description, serve to explain the principles of the disclosure.

BRIEF DESCRIPTION OF THE DRAWINGS

FIG. 6 depicts some aspects of an illustrative embodiment of an apparatus as described herein.

FIG. 7 depicts some aspects of an illustrative embodiment of an apparatus as described herein.

FIG. 8 depicts some aspects of an illustrative embodiment of an apparatus as described herein.

DESCRIPTION OF THE EMBODIMENTS

Figure 1:
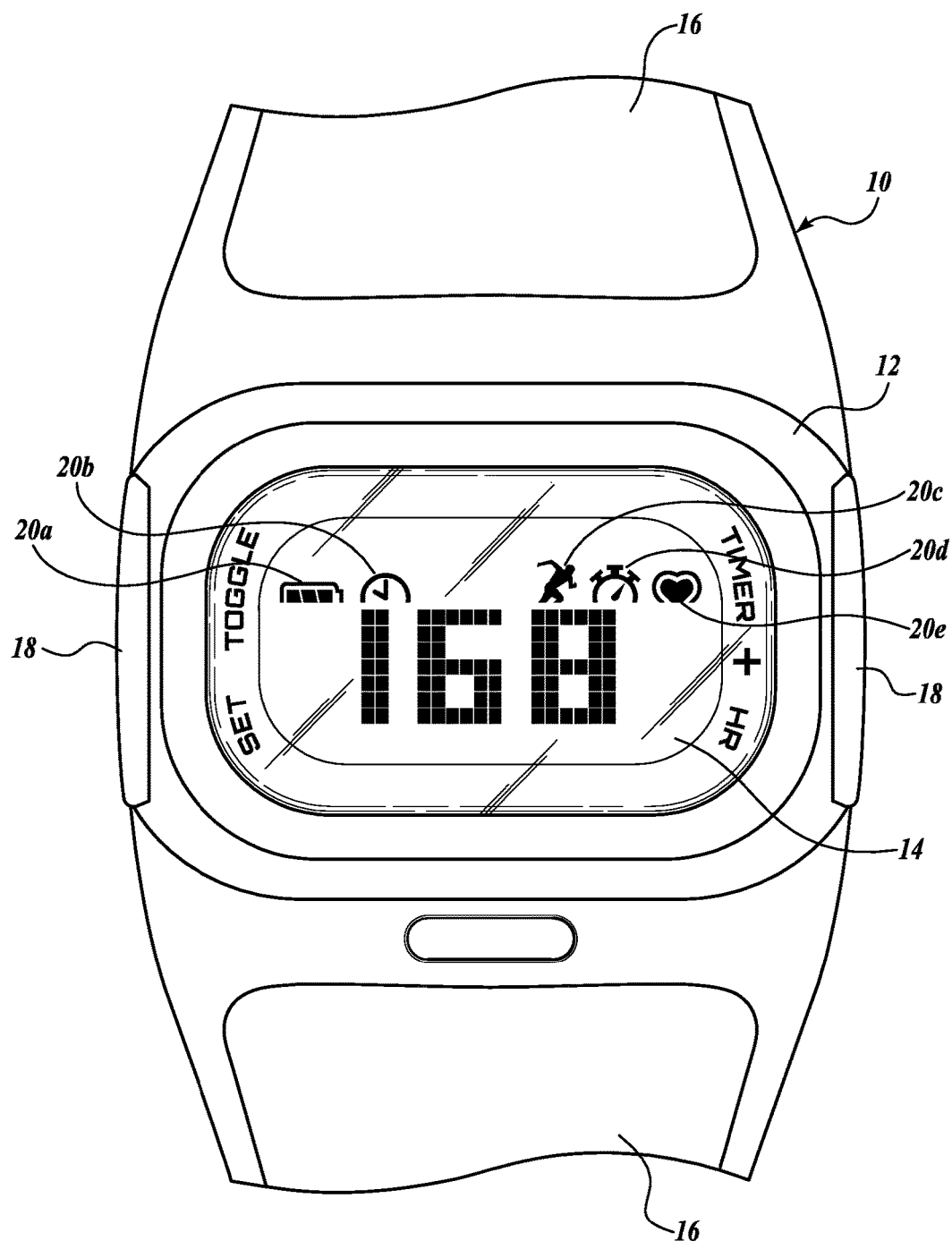
FIG. 1 depicts some aspects of an illustrative embodiment of an apparatus as described herein.

Shown in FIG. 1 is an apparatus 10 comprising an optical sensor and components for processing and displaying a physiological parameter of a user, as well as other information that may or may not be directly related to the user's activity or environment. In one embodiment, the physiological parameter may be heart rate information. In other embodiments, however, other physiological information may be displayed. As depicted in FIG. 1, apparatus 10 may be a watch, however, apparatus 10 may also be a band, strap, or any other wearable device configured for securing to a user's body or an appendage thereof.

In one embodiment, apparatus 10 may house a display unit 14 for displaying or otherwise conveying information to the user. In one embodiment, the display unit 14 may comprise a dot matrix liquid crystal display 14. In alternative embodiments, the display unit 14 may comprise some other suitable display or one or more light sources for conveying information. In still further embodiments, apparatus 10 may comprise no display unit. Rather, information collected, measured, or stored at apparatus 10 may be communicated to the user by some other means, such as wired or wireless transmission to another device or external display.

In another aspect, apparatus 10 may comprise a housing 12 and a pair of bands 16 extending from opposite edges of the housing 12 for securing apparatus 10 to the user. In other embodiments, apparatus 10 may comprise a single band 16 and have no housing. In such embodiments, one or more components of apparatus 10 may be embedded or located within band 16.

In one embodiment, bands 16 may comprise a flexible or rigid elastomeric, plastic, silicone, or polymer material. In alternative embodiments, bands 16 may comprise some other suitable material, including but not limited to, a fabric, woven, or metal material.

Apparatus 10 may further comprise one or more switches 18 operable for accepting input from the user. In one embodiment, switches 18 may extend along the narrow edges of housing 12. In other embodiments, switches 18 may be located elsewhere on housing 12 or along band 16.

In use, the user may manipulate switches 18 for, among other things, establishing an operational mode of apparatus 10, inputting user-specific information such as sex, height, weight, etc., entering a date or time, navigating one or more menus, or inputting other information. In one aspect, switches 18 may comprise any switch, button, or sensor configured to accept input from the user. In alternative embodiments, switches 18 may be incorporated into display unit 14. For example, switches 18 may comprise "soft" buttons configured to accept input from the user via a touchscreen. FIG. 1 depicts a pair of switches 18, one positioned on either side of the housing 12. Other embodiments, however, may comprise fewer or additional switches.

Housing 12 or straps 16 may further comprise switch indicators for providing the user with information regarding each switch. In one embodiment, housing 12 or straps 16 may comprise words and/or symbols such as "set," "toggle," "timer," "+," and "HR" corresponding to the switches and providing the user with an indication of a function to be achieved by manipulation of the respective switch. Of course, the switch indicators depicted in FIG. 1 are only illustrative of the possibilities. Housing 12 or bands 16 may comprise fewer, additional, or alternative indicators.

In an embodiments comprising display unit 14, the display may comprise one or more small icons for conveying information to the user. In one embodiment, the one or more icons may be located in an upper portion of the display 14 to indicate operational and/or conditional aspects of apparatus 10. In the depicted embodiment, icon 20a may be illuminated whenever the watch is energized to indicate battery condition; icon 20b may be illuminated when display 14 indicates the time of day; icon 20c and 20e may be illuminated when apparatus 10 is monitoring, measuring, or displaying physiological parameter information (e.g., heart rate information); and icon 20d may be illuminated when apparatus 10 is operating in an activity mode and/or an activity duration is being recorded. As also is indicated in FIG. 1, physiological parameter information (e.g., the user's heart rate or some other detected or measured parameter) may be displayed in a central region 20f of display 14. The same display region may also display a date, time, or other information when apparatus 10 is in different operational states. Of course, the aforementioned examples of icons 20a-20f and/or each icon's respective size and position within display unit 14 are only illustrative of the possibilities. Fewer, additional, or alternative icons and/or icon size and placement is also possible.

Alternatively or additionally, apparatus 10 may comprise a communication status indicator 21. In one embodiment, the status indicator 21 may comprise an outward facing light source viewable by the user when the watch is in use. In some embodiments, the light source may comprise one or more lights, such as LEDs. In further embodiments, the light source may comprise a plurality of LEDs, each of a different color. In this manner, the color of the LED illuminated may convey additional information to a user regarding the communication status of apparatus 10. For example, when apparatus 10 may be in communication with another device via a suitable communication channel, such as Bluetooth communication, status indicator may illuminate light of a first color. Where apparatus 10 may be in communication with another device via some alternative communication channel, status indicator 21 may illuminate light of a second color. Alternatively, or additionally, status indicator 21 may illuminate light of another color when ongoing communication with another device may be terminated and/or apparatus 10 ends or initiates an operational state. Again, these examples are only illustrative of the possibilities and status indicator 21 may illuminate one or more light sources corresponding to one or more colors to indicate or convey any suitable information to the user. Moreover, in an embodiments of apparatus 10 that do not comprise a display unit 14, status indicator may convey some or all of the information described above with respect to display unit 14.

Figure 2:
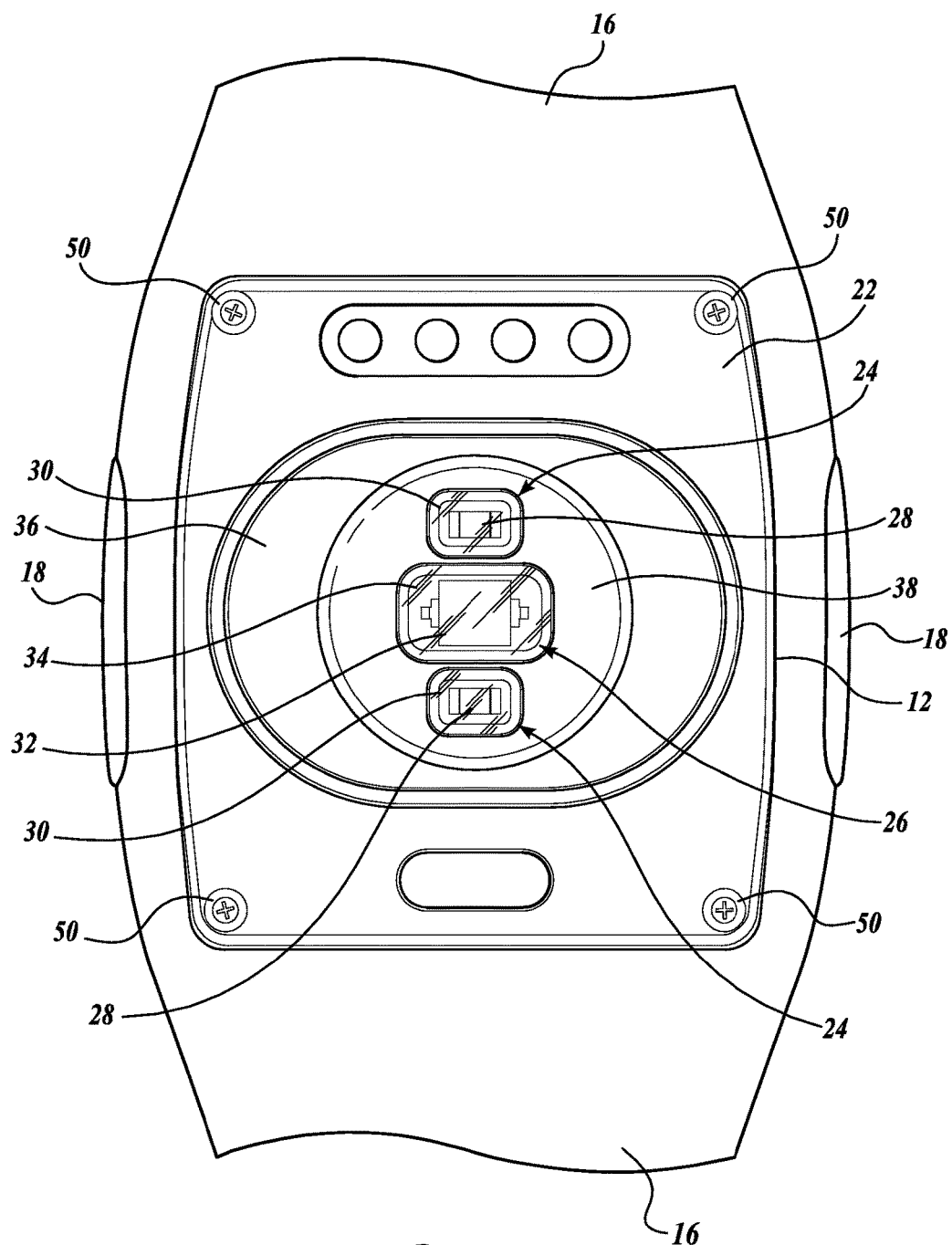
FIG. 2 depicts some aspects of an illustrative embodiment of an apparatus as described herein.

FIG. 2 depicts an embodiment of the back of apparatus 10 comprising a caseback 22. Caseback 22 may be secured to apparatus 10 using any suitable attachment system or method. For example, as depicted in FIG. 2, caseback 22 may be secured to apparatus 10 by one or more screws 50 or some other suitable attachment mechanism. Alternative embodiments may comprise a caseback integrated with straps 16 such that no attachment mechanism is needed. Other embodiments may comprise no caseback at all. Rather, strap 16 may comprise one or more integral or discrete components or structure substantially similar or corresponding to those described below with respect to caseback 22, i.e., where a caseback, structure of a caseback, or a component positioned within a caseback may be described herein, corresponding structure and/or locating of components may be achieved in straps 16 and a caseback may not be necessary.

In one embodiment, caseback 22 may comprise an optical sensor as described herein. Specifically, the optical sensor may comprise one or more light sources. As depicted in FIG. 2, the optical sensor may comprise two light sources 24 that may be spaced apart from one another. Alternative embodiments may comprise fewer or additional light sources. In the depicted arrangement, each light source 24 may include one or more LEDs 28 that may be contained in a respective lens 30. In that regard, it should be noted that lens 30 may not necessarily be the same as, nor replace, the integral lens of a conventional LED, which is configured to cause emitted light to pass from an end surface of the device.

In another aspect, one or more optical detectors 26 may be located between, adjacent, or proximate light sources 24. In one embodiment, the one or more optical detectors may comprise one or more photodiodes 32 that may be contained by a corresponding lens 34.

As depicted in FIG. 2, one or more optical detectors 26 may be positioned between, equidistant, and symmetrically aligned with respect to a pair of light sources 24. Such an embodiment, however, is only illustrative of the possibilities and other suitable configurations are also possible. For example, in other embodiments, optical detector 26 may be fully or partially encircled by one or more light sources 24. Alternatively, optical detector 26 may not be symmetrically situated between the one or more light sources, i.e., optical detector 26 may be positioned closer to one or more light sources than one or more other light sources. In still further embodiments, optical detector 26 may not be located between the two or more light sources. The location and number of optical detectors 26 and light sources 24 may also be reversed from that shown in FIG. 2. For example, the optical sensor may comprise a light source 24 located between, adjacent, or proximate one or more optical detectors 26.

In some embodiments, lenses 30 and 34 may comprise a mineral glass or a plastic that may exhibit a high degree of optical transmission at wavelengths of the optical energy emitted by LEDs 28. In alternative embodiments, lenses 30 and 34 may comprise some other suitable material. In some instances it may be possible to form lens 30 and 34 from material that imparts a filtering effect to the lenses. For example, ambient light that reaches photodiode 32 may be noise that can affect the operation and/or accuracy of apparatus 10. In embodiments in which LEDs 28 emit light sufficiently removed from the infrared region, it may be advantageous to use lenses that block a portion of incident infrared energy to thereby decrease the effect of any ambient light that may pass between caseback 22/strap 16 and the user's tissue. In still further embodiments, one or more of lenses 234 and 244 may comprise an epoxy layer or encasement poured or placed into caseback 220 rather than a glass or plastic lens. Such an epoxy layer may be pre-formed or formed with a respective light source or optical detector positioned within caseback 220. In such embodiments, the epoxy layer may be separated from the respective LED 232 or photodiode 242 by a barrier or by space. Alternatively, the epoxy may completely or partially encase the respective LED 232 or photodiode 242.

In another aspect, caseback 22 may be configured such that the optical sensor may be in contact or urged firmly against the skin when apparatus 10 is worn by a user. In that regard, caseback 22 may comprise a raised region 36 that may project outwardly from the surface of caseback 22.

In some embodiments, centrally located in raised region 36 may be a further raised region 38. The raised and further raised region may serve to adequately urge the optical sensor against the user's skin. As mentioned above, in embodiments that do not comprise a caseback 22, raised region 36 and/or further raised region 38 may be formed in, or attached to, strap(s) 16.

In one aspect, the surface of LED lenses 28 and optical detector lens 34 may be substantially flush with or extend slightly above the surface of the further raised region 38. Of course, in other embodiments, caseback 22 may comprise only one of raised region 36 and further raised region 38. Alternatively, caseback 22 may comprise additional raised regions. Moreover, while FIG. 2 depicts raised region 36 as a substantially elliptical region and further raised region 38 as a substantially circular raise region, other suitable shapes of the raised region and further raised region are possible and the depicted embodiments should not be construed to limit the possibilities.

Figure 3:
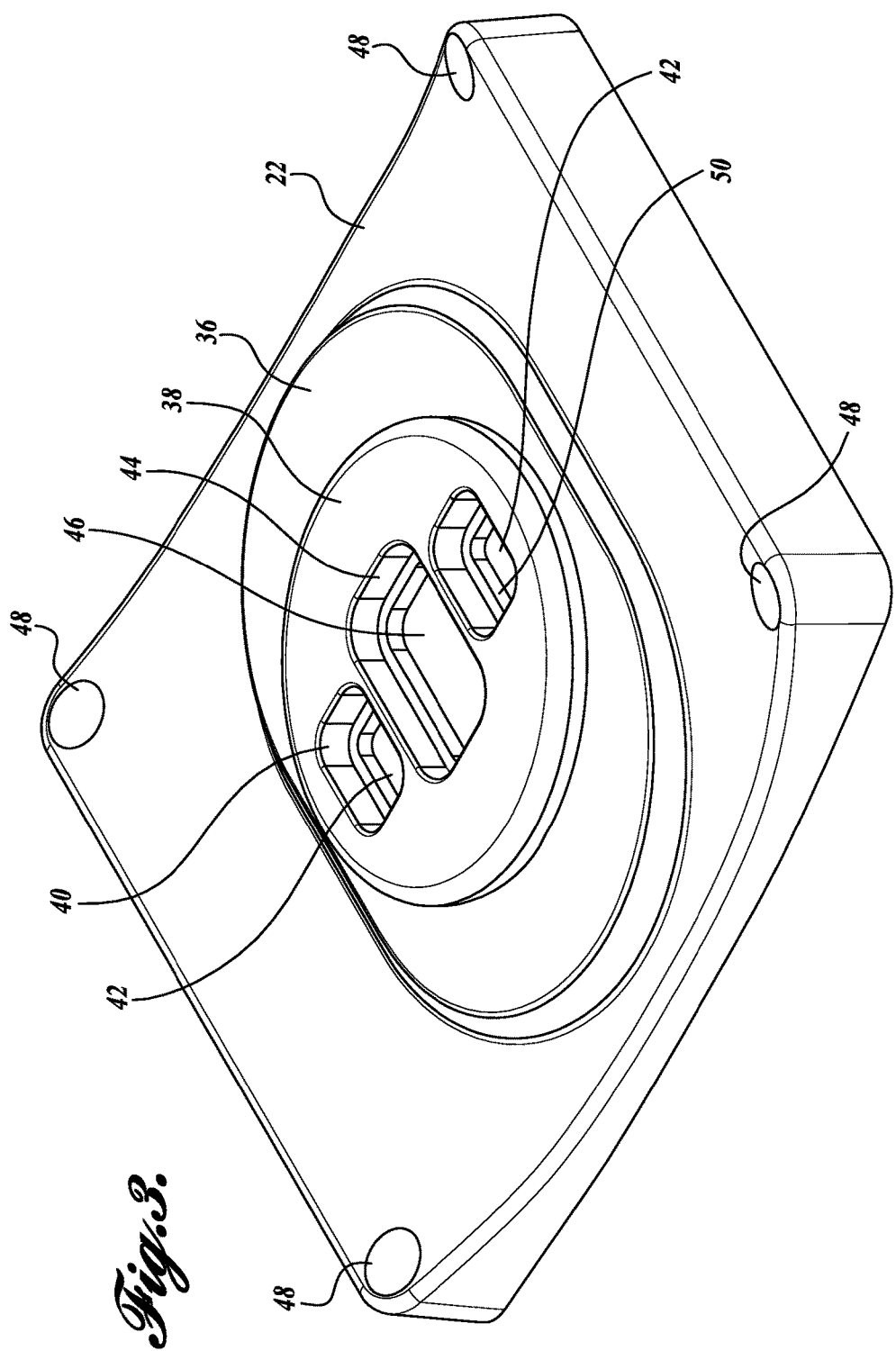
FIG. 3 depicts some aspects of an illustrative embodiment of an apparatus as described herein.
Figure 4:
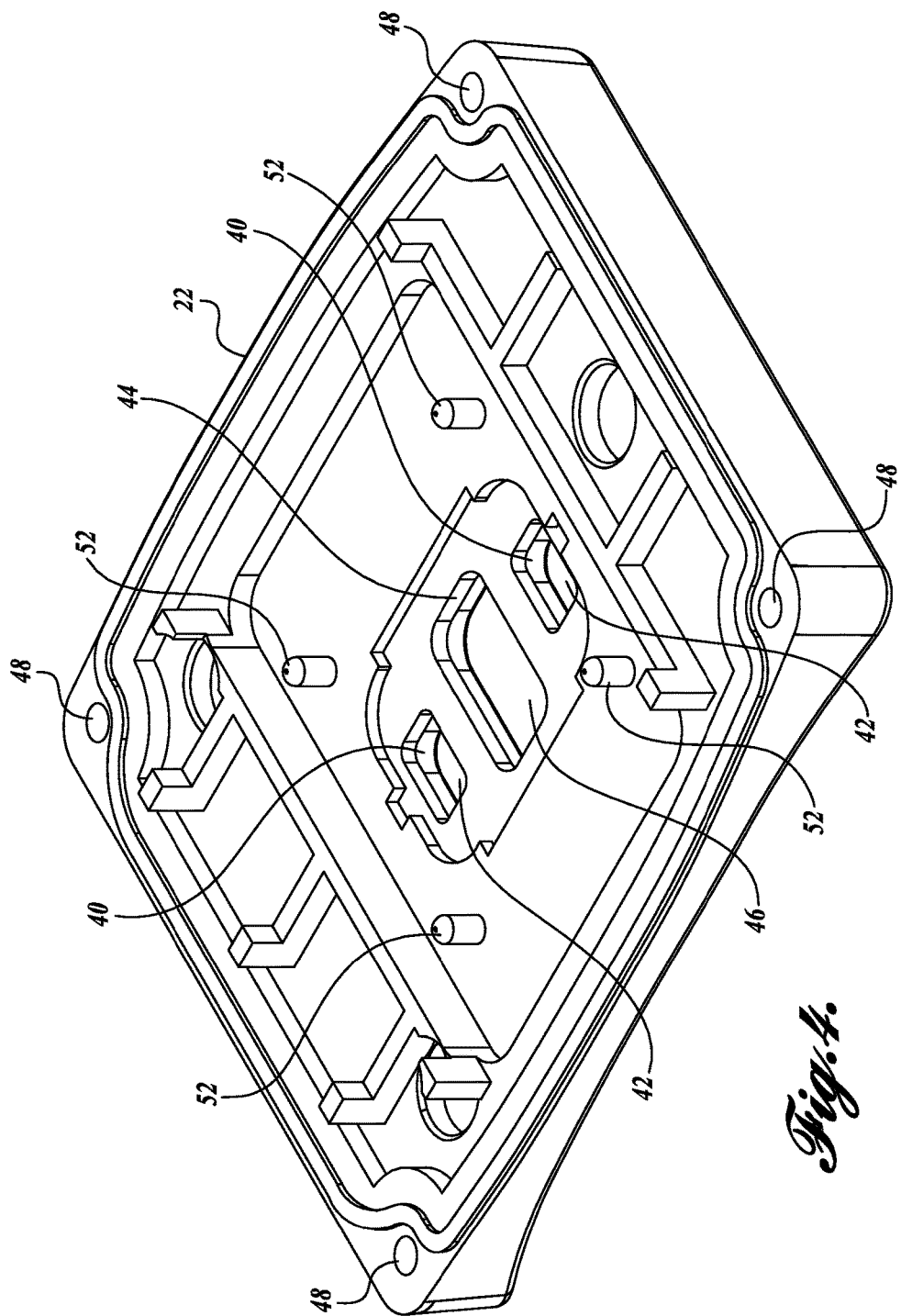
FIG. 4 depicts some aspects of an illustrative embodiment of an apparatus as described herein.

FIGS. 3 and 4 respectively, illustrate the back and interior of caseback 22 prior to the installation of LEDs 28, LED lenses 30, photodiode 32 and optical detector lens 34. Again, in embodiments that do not comprise a caseback 22, some or all of the structure depicted in FIGS. 3 and 4 may be formed in, or attached to, strap(s) 16. For example, in one embodiment, strap(s) 16 may comprise a pair of adjacent layers, one or both of which may comprise some or all of the structure depicted in FIGS. 3 and 4. The layers may then be attached, joined, or adhered to one another in any suitable manner to create a structure substantially similar to that described herein with respect to caseback 22 and the remainder of apparatus 10.

As can be seen in both FIGS. 3 and 4, recesses 40 may extend inwardly into the back of caseback 22 for receiving LED lenses 30. The interior of each recess 40 may be shaped to substantially correspond with the exterior configuration of a lens 30. An opening 42 may be located at the bottom of each recess 40 for receiving an LED 28. Each opening 42 may be smaller than the cross-sectional area of the associated recess 40 so that an inwardly-extending ledge may be formed around the lower periphery of the recess 40. When an LED lens 30 is inserted in the recess 40, the bottom of the lens may come into abutment with the ledge and the face of the lens may be flush with, or project slightly beyond, the rear face of caseback 22.

Similarly, a recess 44 may extend inwardly in caseback 22 for receiving optical detector lens 34. The configuration of recess 44 may correspond to that of recesses 40 in that the interior wall of recess 44 may be configured to substantially correspond with the exterior configuration of optical detector lens 34. An opening 46 may be located at the bottom of recess 44 for receiving optical detector lens 43. Opening 46 may be smaller than the cross-sectional area of recess 44 so that an inwardly extending ledge may be formed around the lower periphery of recess 44. When an optical detector lens 34 is inserted in the recess 44, the bottom of the lens may come into abutment with the ledge and the face of the lens may be flush with, or project slightly beyond, the rear face of caseback 22.

In view of FIGS. 3 and 4, it may be recognized that recesses 40 and 44 may establish the position of LED lenses 30 relative to optical detector lens 34. This, in turn, may establish the distance and positional relationship between LEDs 28 and photodiode(s) 32. In practice, recesses 40 and 44 may be positioned to ensure that sufficient light emitted by LEDs 28 may reach photodiode 32 after being reflected by the user's body (e.g., blood flowing through arteries and other vascular structure). As described previously, the particular location of recesses 40 and 44, as shown in FIGS. 3 and 4 is only illustrative and other suitable locations may be possible.

As also can be seen in FIG. 3, the rear face of caseback (or strap(s) 16, in embodiments with no caseback) may be contoured to substantially correspond with the wrist or forearm of the user. In one embodiment, openings 48 may be located in each corner of caseback 22 for threaded fasteners 50 (depicted in FIG. 2) that may secure caseback 22 to case 12 of FIG. 1. Additionally, as shown in FIG. 4, four placement posts 52 may extend from caseback 22 to ensure proper placement of a circuit board comprising one or more of LEDs 28 and photodiode(s) 32. Proper placement of the circuit board may, in turn, ensure proper positioning of the LEDs and/or photodiode(s) with respect to caseback 22 and/or corresponding LED lenses 30 and/or optical detector lens 34. In one embodiment, placement posts 52 may be cylindrical in shape and may be located so as to form a rectangular pattern extending toward the interior of caseback 22. In alternative embodiments, placement posts 52 may exhibit some other suitable shape and/or may be positioned in another arrangement for ensuring proper positioning of the circuit board, LEDs 28, and/or photodiode 32.

Figure 5:
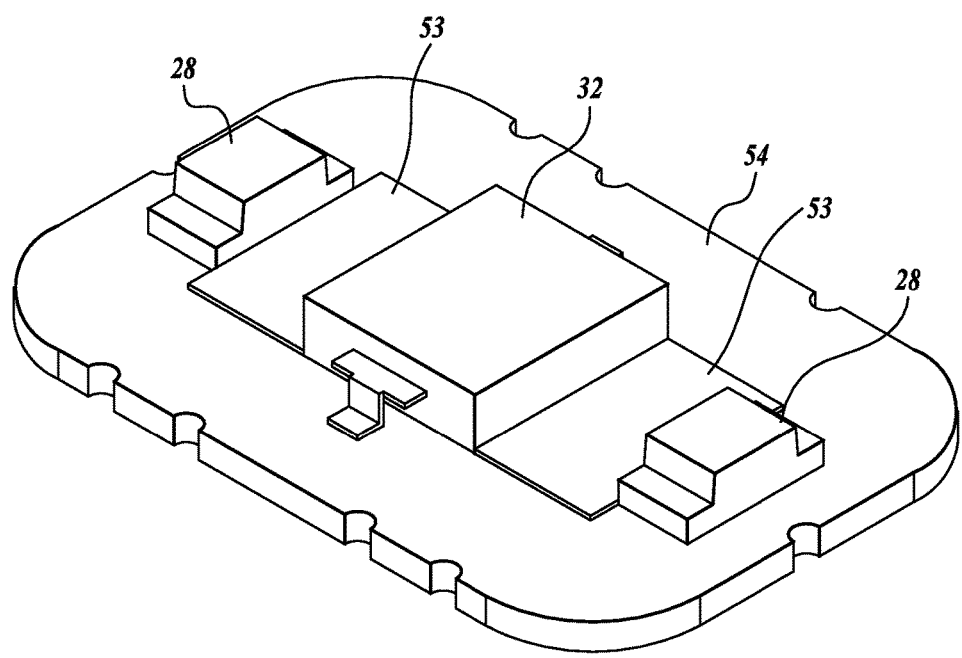
FIG. 5 depicts some aspects of an illustrative embodiment of an apparatus as described herein.

FIG. 5 depicts an arrangement for mounting LEDs 28 and photodiode 32. In the depicted arrangement, LEDs 28 and photodiode 32 may be positioned relative to one another by means of a printed circuit board 54 that electrically connects the devices to other circuitry contained in apparatus 10 (not shown). In one embodiment, a relatively thin strip of opaque pliant material 53 (such as, but not limited to, a tape, a sponge-like polymer, or an epoxy) may extend between the edges of photodiode 32 and the adjacent edges of LEDs 28. As described relative to the assembled caseback (FIGS. 7 and 8) opaque strips 53 may prevent light emitted by the LEDs from travelling along the surface of printed circuit board 54 and reaching photodiode(s) 32.

Although FIG. 5 depicts LEDs 28 and photodiode 32 on a single circuit board, alternative embodiments comprising a plurality of circuit boards in communication with one another are also possible. In such embodiments, commands to and/or measurements from LEDs 28 and photodiode(s) 32 may be communicated via one or more wired or wireless communication channels.

FIG. 6 is a partially cutaway view of caseback 22 and printed circuit board 54 that illustrates one possible manner in which the optical sensor may be incorporated in caseback 22 (or strap(s) 16 in embodiments that do not comprise a caseback). In FIG. 6, LED lenses 30 may be inserted and sealed in recesses 42 of FIGS. 3 and 4. As previously indicated, the light-emitting surface of each lens 30 may be substantially flush with, or extend slightly above, the surface of further raised region 38.

In a like manner, optical detector lens 34 may be inserted and sealed in recess 44 of FIGS. 3 and 4. The light-receiving surface of lens 34 may be substantially flush with, or extend slightly above, the surface of further raised region 38. Various techniques can be used for bonding LED lenses 30 and optical detector lens 34 to caseback 22. For example, depending in part of the material being used for caseback 22 or strap(s) 16, the lenses may be bonded in place by a curable adhesive, ultrasonic bonding or other techniques. In some applications, insert molding or cold-molding techniques may be employed. As indicated by phantom lines in FIG. 6, LEDs 28 and photodiode(s) 32 may pass into openings 42 and 44 so that LEDs 28 may be at least partially contained or received by lenses 42 and photodiode(s) 32 may be at least partially contained or received by optical detector lens 34.

Lenses such as those depicted in FIGS. 2 and 6-8 may be advantageous with respect to product manufacture, eliminating the prior use of a transparent epoxy resin to encapsulate the sensor elements in openings formed in the rear face of the watch. Not only may device assembly be simplified, but the process of device and/or component repair may be made more efficient. Moreover, light transmission through one or more lenses may be superior (i.e., less loss, noise, scatter, etc.) to light transmission through an epoxy. This, in turn, may enhance overall device performance, including the emitting and detecting of light to and from a targeted area. In some embodiments, the protrusion height of one or more raised region 36 and further raised region 38 may be less pronounced or protrude a shorter distance from the device where glass or plastic lenses are used.

FIG. 7 depicts a cross-sectional view of one embodiment of apparatus 10 comprising caseback 22, LEDs 28, photodiode 32 and the associated lenses 30 and 34. As can be seen in FIG. 7, printed circuit board 54 (described relative to FIGS. 5 and 6) may be positioned on the upper surface of a circuit board 56. In one embodiment, circuit board 56 may include circuitry for detecting and displaying one or more physiological parameters of a user (e.g., a user's heart rate), the time of day and other information (not shown). Mounting posts 52, extending from caseback 22 and through or about circuit boards 54 and 56 (FIG. 4) may maintain circuit boards 54 and 56 in a fixed position within caseback 22. LEDs 28 may extend into corresponding lenses 30 and photodiode 32 may extend into corresponding photo detector lens 34. In other embodiments, circuit board 56 may not be positioned below printed circuit board 54. Rather, circuit board 56 may be located at another position along the longitudinal extension of strap(s) 16. In such embodiments, printed circuit board 54 and circuit board 56 may be in communication with one another through a suitable wired or wireless communication channel. In alternative embodiments, apparatus 10 may not comprise a second circuit board.

FIG. 7, alone and in combination with FIG. 8, may illustrate optical isolation of photodiode 32 from LEDs 28. As described relative to FIG. 3, the openings 42 for receiving LEDs 28 may be smaller than the recesses 40 for receiving LED lenses 30. Likewise, the opening 46 for receiving photodiode 32 may be smaller than the recess 44 for receiving the optical detector lens 34. In this manner, each combination of LED 28 and LED lens 30 may be physically and optically separated from the combination of photodiode 32 and optical detector lens 34 by a respective barrier 58 that may extend downwardly from further raised region 38 of caseback 22 to the base of the LEDs 28 and photodiode 32. In one embodiment, each barrier 58 may comprise an inverted T-shaped barrier. As is shown in FIG. 7, the inner edges of LED lenses 30 may be separated from the outer edges of optical detector lens 34 by an upwardly extending leg of the T-shaped barrier 58 and the inner edges of LEDs 28 may be separated from the outer edges of photodiode 32 by a laterally extending lower leg of the T-shaped barrier 58. In addition, the bottom surface of laterally extending lower leg of each T-shaped barrier 58 may contact and/or press against the opaque strips 53 (shown and described relative to FIG. 5) to further ensure that light emitted by LEDs 28 does not reach photodiode 32 without being reflected by a targeted region of the user.

While illustrative embodiments have been illustrated and described, it will be appreciated that various changes can be made therein without departing from the spirit and scope of the disclosure. For example, those skilled in the art will recognize that the disclosure can be practiced with a variety of physiological monitoring devices and that various light emitting and photo detecting devices may be employed. In some situations it may be appropriate to use one or more lenses that are configured for receiving more than one optical sensor in a single lens and/or to use one or more lenses that are configured for receiving more than one light source in a single lens. Furthermore, while some figures described herein may depict a watch-like embodiment, other embodiments may comprise fewer, additional, or alternative features similar to common fitness bands and/or other wearable devices for monitoring physiological information, including bands comprising a single strap or devices that may or may not comprise a display unit for displaying alphanumeric information.

It is intended that this specification and the aforementioned examples and embodiments be considered as illustrative only, with the true scope and spirit of the disclosure being indicated by the following claims.

What is claimed is:

1. An apparatus for sensing and measuring at least one physiological parameter of a person, the apparatus comprising:
    at least a portion of the apparatus configured for contacting a targeted tissue region;
    an optical sensor comprising at least one light source for illuminating the targeted tissue region and at least one optical detector for receiving optical energy reflected from the targeted tissue region, the at least one light source and the at least one optical detector being coupled to a substrate,
    at least one lens associated with the at least one light source that directs light to the targeted tissue region;
    at least one lens associated with the at least one optical detector that passes light reflected from the targeted tissue region; and
    at least one barrier optically separating the at least one light source and the at least one optical detector wherein the at least one barrier is "T-shaped" and comprises a laterally-extending portion coupled to the substrate and a vertically-extending portion extending from the laterally-extending portion toward the targeted tissue region, the laterally-extending portion and the vertically-extending portion each optically separating the at least one light source and the at least one optical detector,
    wherein each lens is located in the portion of the apparatus contacting the targeted tissue region.

2. The apparatus of claim 1, wherein each light source and each optical detector is associated with, and at least partially contained by, a separate associated lens that individually couples light between the optical sensor and the targeted tissue region.

3. The apparatus of claim 2, further comprising a front face, a rear face, and an interior region defined between the front and rear faces, the interior region comprising the optical sensor,
    wherein each lens is at least partially positioned in an associated opening that extends through the rear face so that light is coupled between the optical sensor and the targeted tissue region.

4. The apparatus of claim 3, wherein the targeted tissue region is located on a person's arm and the apparatus is configured to be worn with at least a portion of the rear face in contact with the person's arm.

5. The apparatus of claim 4, wherein each light source is a light emitting diode and each optical detector is a photodiode.

6. The apparatus of claim 5, wherein each lens includes a recess sized for at least partially containing the light emitting diode or photodiode associated with the respective lens.

7. A device for monitoring at least one physiological parameter of a person, the device comprising:
    an elongate body comprising a front face, a rear face, and an interior region defined between the front and rear faces, at least a portion of the rear face configured for contacting a targeted area of a person's body;
    an optical sensor comprising at least one light source for illuminating at least a portion of the targeted area and at least one optical detector for receiving reflected light from the targeted area, the at least one light source and the at least one optical detector being coupled to a substrate;
    at least one lens associated with the at least one light source for allowing light to pass between the at least one light source and the targeted area;
    at least one lens associated with the at least one optical detector for allowing light to pass between the at least one optical detector and the targeted area;

and at least one barrier optically separating the at least one light source and the at least one optical detector, the at least one barrier being "T-shaped," comprising a laterally-extending portion located adjacent the substrate and on a same side of the substrate as the at least one light source and the at least one optical detector and a vertically-extending portion extending from the laterally-extending portion to the targeted area, each portion optically separating the at least one light source and the at least one optical detector.

8. The device of claim 7, wherein each light source and each optical detector is associated with a dedicated lens that allows light to pass between the optical sensor and the targeted area.

9. The device of claim 8 wherein the targeted area is located on a person's arm.

10. The device of claim 9, wherein the rear face comprises a plurality of openings, each opening configured to receive a respective one of the lenses, each lens comprising at least a portion configured for contact with the targeted area.

11. The device of claim 10, wherein each lens comprises a cavity for at least partially receiving an associated light source or optical detector.

12. The device of claim 11 further comprising at least one circuit board, the circuit board contained within the interior region in spaced apart juxtaposition with the rear face, each light source and optical detector being mounted to the at least one circuit board and extending into the cavity of an associated lens.

13. The device of claim 7, wherein the the at least one light source comprises a pair of light sources spaced apart from one another, the at least one optical detector being positioned at least partially between the pair of light sources.

14. The device of claim 7 further comprising circuitry for processing a signal supplied by the optical detector and for communicating the at least one physiological parameter to a user.

15. A wearable apparatus for monitoring at least one physiological parameter, the apparatus comprising:

a body comprising a front face, a rear face, and an interior region defined between the front and rear face;

one or more light emitters, each operable for directing light energy toward a targeted area of a user's body;

one or more optical detectors, each operable for producing an electrical signal representative of light detected at that optical detector;

a substrate to which the one or more light emitters and one or more optical detectors are electrically coupled at least one barrier optically separating a first of the one or more light emitters and a first of the one or more optical detectors, wherein the at least one barrier is "T-shaped" and comprises a laterally-extending portion proximate the substrate and on a same side of the substrate as the first of the one or more light emitters and the first of the one or more optical detectors, and a vertically-extending portion extending between the laterally-extending portion and the targeted area, each portion optically separating the first light emitter and the first optical detector.

16. The apparatus of claim 15 wherein the one or more light emitters comprises a pair of light emitters spaced apart from one another, the at least one optical detector being located at least partially between the pair of light emitters.

* * * * *